US00PP33010P2

(12) United States Plant Patent
Noordhuis et al.

(10) Patent No.: US PP33,010 P2
(45) Date of Patent: Apr. 27, 2021

(54) ***DELPHINIUM* PLANT NAMED 'ET DLP 17-14'**

(50) Latin Name: ***Delphinium elatum* X *(Delphinium* x *belladonna)***
Varietal Denomination: ET DLP 17-14

(71) Applicants: Bart Noordhuis, Boijl (NL); Elisabeth Bisschop, Boijl (NL)

(72) Inventors: Bart Noordhuis, Boijl (NL); Elisabeth Bisschop, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 0 days.

(21) Appl. No.: 16/873,747

(22) Filed: Jun. 23, 2020

(30) Foreign Application Priority Data

Nov. 1, 2019 (QZ) ..... PBR 2019/2772

(51) Int. Cl.
*A01H 5/02* (2018.01)
*A01H 6/72* (2018.01)

(52) U.S. Cl.
USPC ..... Plt./423

(58) Field of Classification Search
USPC ..... Plt./423
See application file for complete search history.

*Primary Examiner* — Susan McCormick Ewoldt
(74) *Attorney, Agent, or Firm* — C. Anne Whealy

(57) ABSTRACT

A new and distinct cultivar of *Delphinium* plant named 'ET DLP 17-14', characterized by its relatively compact, upright and sturdy plant habit; relatively small dark green-colored leaves; freely flowering habit; strong flowering stems with dense inflorescences with numerous light purple-colored flowers; and good garden performance.

2 Drawing Sheets

Figure 1:
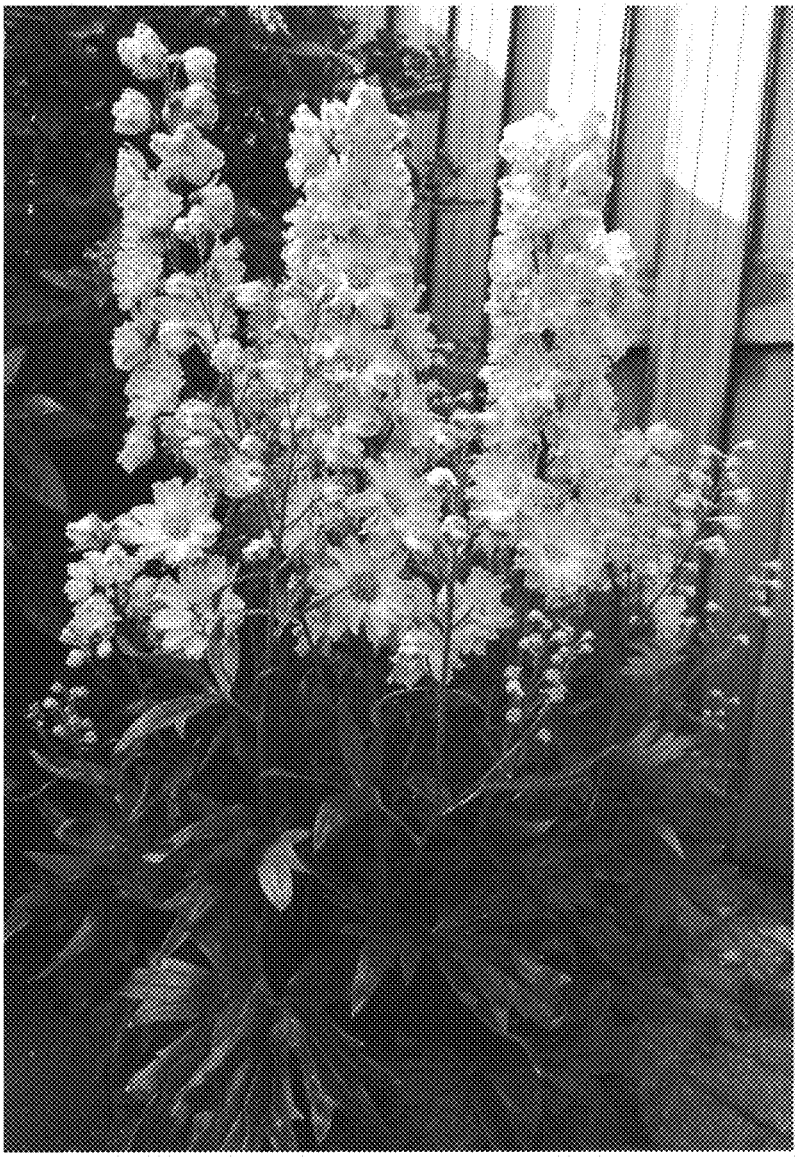

Botanical designation: *Delphinium elatum* X (*Delphinium* x *belladonna*).

Cultivar denomination: 'ET DLP 17-14'.

CROSS-REFERENCE TO A RELATED APPLICATION AND STATEMENT REGARDING PRIOR DISCLOSURES BY INVENTORS/APPLICANTS

This application claims priority to a European Community Plant Breeders' Rights application filed on Nov. 1, 2019, application number 2019/2772. There have been no offers for sale anywhere in the world prior to the effective filing date of this Application and no accessibility to one of ordinary skill in the art could have been derived from the printed Plant Breeder's Rights documents.

The Inventors/Applicants assert that no publications nor advertisements relating to sales, offers for sale or public distribution occurred more than one year prior to the effective filing date of this application. Any information about the claimed plant would have been obtained from a direct or indirect disclosure from the Inventors/Applicants. Inventors/Applicants claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Delphinium* plant, botanically known as *Delphinium elatum* X (*Delphinium* x *belladonna*), typically grown as a perennial garden plant and hereinafter referred to by the name 'ET DLP 17-14'.

The new *Delphinium* plant is a product of a planned breeding program conducted by the Inventors in Boijl, The Netherlands. The objective of the breeding program is to create new relatively compact and strong *Delphinium* plants with dense inflorescences and unique and attractive flower colors.

The new *Delphinium* plant originated from a cross-pollination in July, 2012 of a proprietary selection of *Delphinium elatum* identified as code number 1132, not patented, as the female, or seed, parent with a proprietary selection of *Delphinium* x *belladonna* identified as code number 622, not patented, as the male, or pollen, parent. The new *Delphinium* plant was discovered and selected by the Inventors as a single flowering plant from within the progeny of the stated cross-pollination in a controlled greenhouse environment in Boijl, The Netherlands in July, 2012.

Asexual reproduction of the new *Delphinium* plant by in vitro meristem culture in a controlled environment in Boijl, The Netherlands, since August, 2016 has shown that the unique features of this new *Delphinium* plant are stable and reproduced true to type in successive generations.

SUMMARY OF THE INVENTION

Plants of the new *Delphinium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ET DLP 17-14'. These characteristics in combination distinguish 'ET DLP 17-14' as a new and distinct *Delphinium* plant:

1. Relatively compact, upright and sturdy plant habit.
2. Relatively small dark green-colored leaves.
3. Freely flowering habit.

4. Strong flowering stems with dense inflorescences with numerous light purple-colored flowers.
5. Good garden performance.

Plants of the new *Delphinium* differ primarily from plants of the female parent selection in the following characteristics:

1. Plants of the new *Delphinium* have shorter and stronger upright flowering stems than plants of the female parent selection.
2. Plants of the new *Delphinium* have denser foliage than plants of the female parent selection.
3. Flowering stems of plants of the new *Delphinium* are branching whereas flowering stems of plants of the female parent selection are not branching.

Plants of the new *Delphinium* differ primarily from plants of the male parent selection in the following characteristics:

1. Plants of the new *Delphinium* have shorter and stronger upright flowering stems than plants of the male parent selection.
2. Plants of the new *Delphinium* are more compact than plants of the male parent selection.
3. Flowering stems of plants of the new *Delphinium* are branching whereas flowering stems of plants of the male parent selection are not branching.

Plants of the new *Delphinium* can be compared to plants of *Delphinium elatum* 'Flamingo Star', not patented. In side-by-side comparisons, plants of the new *Delphinium* differ primarily from plants of 'Flamingo Star' in the following characteristics:

1. Plants of the new *Delphinium* are more compact than plants of 'Flamingo Star'.
2. Plants of the new *Delphinium* have stronger flowering stems than plants of 'Flamingo Star'.
3. Flowering stems of plants of the new *Delphinium* are branching whereas flowering stems of plants of 'Flamingo Star' are not branching.

BRIEF DESCRIPTION OF THE PHOTOGRAPHS

The accompanying colored photographs illustrate the overall appearance of the *Delphinium* plant showing the colors as true as it is reasonably possible to obtain in colored reproductions of this type. Colors in the photographs may differ slightly from the color values cited in the detailed botanical description which accurately describe the actual colors of the new *Delphinium* plant.

The photograph on the first sheet (FIG. 1 of 2) comprises a side perspective view of a typical flowering plant of 'ET DLP 17-14' grown in an outdoor nursery.

Figure 2:
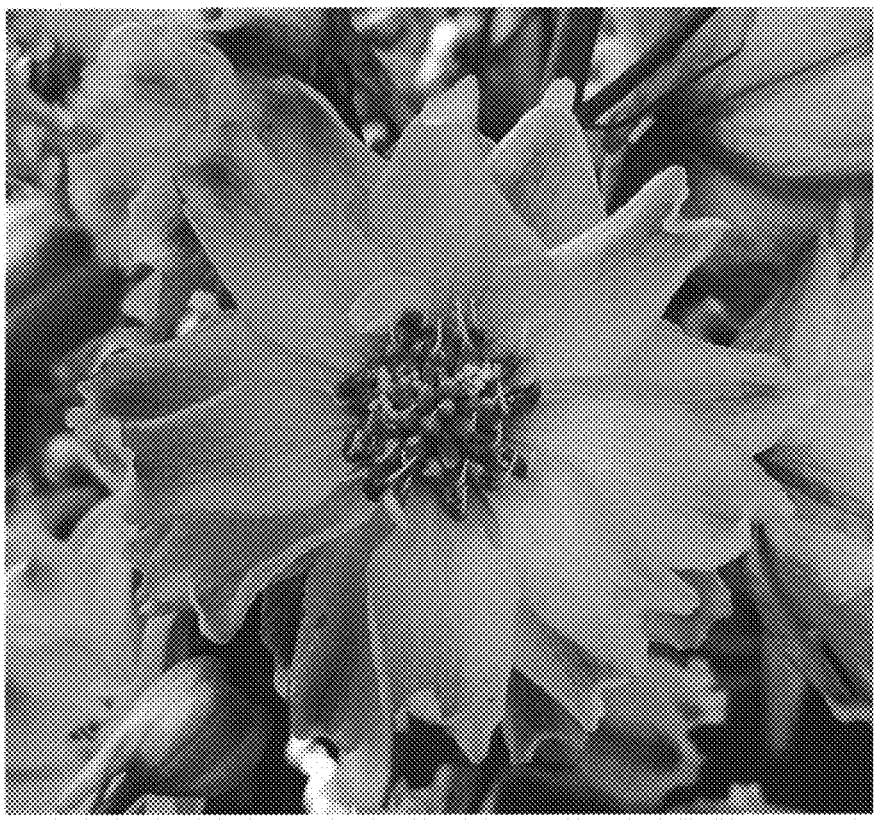

The photograph on the second sheet (FIG. 2 of 2) is a close-up view of a typical flower of 'ET DLP 17-14'.

DETAILED BOTANICAL DESCRIPTION

Plants used for the following description were grown in ground beds and 26-cm containers during the spring and summer in an outdoor nursery in Boijl, The Netherlands and under cultural practices typical of commercial *Delphinium* production. During the production of the plants, day temperatures ranged from 18° C. to 23° C. and night temperatures ranged from 10° C. to 16° C. Plants were one year old when the photographs and the description were taken. In the following description, color references are made to The Royal Horticultural Society Colour Chart, 2001 Edition, except where general terms of ordinary dictionary significance are used.

Botanical classification: *Delphinium elatum* X (*Delphinium* x *belladonna*) 'ET DLP 17-14'.

Parentage:

*Female, or seed, parent*.—Proprietary selection of *Delphinium elatum* identified as code number 1132, not patented.

*Male, or pollen, parent*.—Proprietary selection of *Delphinium* x *belladonna* identified as code number 622, not patented.

Propagation:

*Type of propagation*.—In vitro meristem culture.

*Time to initiate roots, summer*.—About 12 to 16 days at temperatures ranging from 15° C. to 21° C.

*Time to initiate roots, winter*.—About 15 to 25 days at temperatures ranging from 12° C. to 15° C.

*Time to produce a rooted young plant, summer*.—About four weeks at temperatures ranging from 18° C. to 21° C.

*Time to produce a rooted young plant, winter*.—About five to six weeks at temperatures ranging from 12° C. to 15° C.

*Root description*.—Medium in thickness, fibrous; typically close to 11A in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Relatively compact, upright and sturdy plant habit; moderately vigorous to vigorous growth habit and moderate growth rate; freely branching habit.

*Plant height*.—About 60 cm.

*Plant width*.—About 40 cm to 50 cm.

Leaf description:

*Arrangement*.—Alternate or whorled towards the plant base.

*Length*.—About 6 cm to 10 cm.

*Width*.—About 10 cm to 15 cm.

*Shape*.—Palmately lobed with three to five lobes per leaf.

*Apex*.—Acute.

*Base*.—Cordate.

*Margin*.—Entire and incised.

*Texture, upper surface*.—Slightly pubescent; smooth.

*Texture, lower surface*.—Slightly pubescent; rough.

*Venation pattern*.—Palmate.

*Color*.—Developing and fully expanded leaves, upper surface: Close to 137A; venation, close to 144C. Developing and fully expanded leaves, lower surface: Close to 138B; venation, close to 144C.

*Petioles*.—Length: About 5 cm to 10 cm. Diameter: About 2 mm to 5 mm. Strength: Strong. Texture, upper and lower surfaces: Pubescent; smooth. Color, upper and lower surfaces: Close to 144B.

Flower description:

*Flower arrangement and shape*.—Double star-shaped flowers arranged on dense terminal racemes; flowers face mostly outwardly.

*Flowering habit*.—Freely flowering habit with about 20 to 30 flowers developing per inflorescence and more than 500 flowers per plant.

*Fragrance*.—None detected.

*Natural flowering season*.—Long flowering period; plants flower continuously during the spring and summer in The Netherlands.

*Flower longevity*.—Flowers last about two weeks on the plant; flowers not persistent.

*Flower buds*.—Length: About 1 cm to 3 cm. Diameter: About 1 cm to 2 cm. Shape: Ovate. Texture: Smooth, glabrous. Color: Close to 145D.

*Inflorescence height*.—About 25 cm to 35 cm.

*Inflorescence diameter*.—About 8 cm to 10 cm.

*Flower diameter*.—About 4 cm to 5 cm.

*Flower height*.—About 2.5 cm.

*Petals*.—Quantity and arrangement: About three to five crowded in the center of the flower. Length: About 1.5 mm. Width: About 0.75 mm. Shape: Roughly obovate; concave. Apex: Obtuse. Base: Attenuate. Margin: Entire; undulate. Texture, upper and lower surfaces: Smooth, glabrous; satiny. Color: When opening, upper and lower surfaces: Close to 76B; towards the margins, close to 76A; towards the apex, faintly tinged with close to 145A. Fully opened, upper and lower surfaces: Close to 76A; towards the apex, faintly tinged with close to 145A; color does not change with development.

*Sepals*.—Quantity and arrangement: About 15 to 20 arranged in several whorls. Length: About 2 cm. Width: About 1.5 cm to 2 cm. Shape: Obovate; concave. Apex: Obtuse. Base: Attenuate. Margin: Entire; undulate. Texture, upper and lower surfaces: Smooth, glabrous; satiny. Color: When opening, upper and lower surfaces: Close to 76B; towards the margins, close to 76A; towards the apex, faintly tinged with close to 145A. Fully opened, upper and lower surfaces: Close to 76A; towards the apex, faintly tinged with close to 145A; color does not change with development.

*Peduncles*.—Length: About 55 cm. Diameter: About 1 cm. Aspect: Erect. Strength: Strong. Texture: Smooth, glabrous. Color: Close to 144B to 144C.

*Pedicels*.—Length: About 2 cm to 3 cm. Diameter: About 2 mm to 5 mm. Aspect: About 45° from peduncle axis. Strength: Moderately strong. Texture: Smooth, glabrous. Color: Close to 144B to 144C.

*Reproductive organs*.—Stamens: Quantity per flower: About 25 to 30. Filament length: About 1 mm to 2 mm. Filament color: Close to 155D. Anther shape: Oblong. Anther length: About 1 mm to 2 mm. Anther color: Close to 1A to 1D. Pollen amount: None observed. Pistils: Quantity per flower: Five. Pistil length: About 6 mm to 12 mm. Stigma shape: Rounded. Stigma color: Close to 155D. Style length: About 1 mm to 3 mm. Style color: Close to 155D.

*Seeds and fruits*.—To date, seed and fruit development have not been observed on plants of the new *Delphinium*.

Pathogen & pest resistance: To date, plants of the new *Delphinium* have not been noted to be resistant to pathogens and pests common to *Delphinium* plants.

Garden performance: Plants of the new *Delphinium* have exhibited good garden performance and to be tolerant to rain, wind and temperatures ranging from −20° C. to 40° C.

It is claimed:

1. A new and distinct *Delphinium* plant named 'ET DLP 17-14' as illustrated and described.

* * * * *